United States Patent [19]
Jones et al.

[11] Patent Number: 6,030,381
[45] Date of Patent: Feb. 29, 2000

[54] COMPOSITE DIELECTRIC COATING FOR ELECTROSURGICAL IMPLEMENTS

[75] Inventors: Richard F. Jones, Winnetka, Ill.; Michael Henderson, Indianapolis, Ind.

[73] Assignee: MediCor Corporation, Vernon Hills, Ill.

[21] Appl. No.: 09/007,704

[22] Filed: Jan. 15, 1998

Related U.S. Application Data

[63] Continuation of application No. 08/210,354, Mar. 18, 1994, abandoned.

[51] Int. Cl.⁷ .................................................... A61B 17/36
[52] U.S. Cl. ................................ 606/41; 606/45; 606/49; 606/33
[58] Field of Search ................................ 606/41, 45, 49, 606/33

[56] References Cited

U.S. PATENT DOCUMENTS

| | | |
|---|---|---|
| 3,149,175 | 9/1964 | Pollart . |
| 3,246,627 | 4/1966 | Loeb et al. . |
| 3,288,728 | 11/1966 | Gorham . |
| 3,301,707 | 1/1967 | Loeb et al. . |
| 3,318,790 | 5/1967 | Carbajal, III et al. . |
| 3,342,754 | 9/1967 | Gorham . |
| 3,399,124 | 8/1968 | Gilch . |
| 3,600,216 | 8/1971 | Stewart . |
| 3,908,046 | 9/1975 | Fitzpatrick et al. . |
| 4,123,308 | 10/1978 | Nowlin et al. . |
| 4,176,209 | 11/1979 | Baker . |
| 4,225,647 | 9/1980 | Parent . |
| 4,291,244 | 9/1981 | Beach et al. . |
| 4,291,245 | 9/1981 | Nowlin et al. . |
| 4,495,889 | 1/1985 | Riley . |
| 4,500,562 | 2/1985 | Jahn et al. . |
| 4,518,623 | 5/1985 | Riley . |
| 4,572,846 | 2/1986 | Foss et al. . |
| 4,693,927 | 9/1987 | Nishikawa et al. . |
| 4,726,368 | 2/1988 | Morris ..................................... 606/151 |
| 4,921,723 | 5/1990 | Nichols et al. . |
| 4,957,602 | 9/1990 | Binder et al. . |
| 5,024,879 | 6/1991 | Massa et al. . |
| 5,125,927 | 6/1992 | Belanger ..................... 606/45 |
| 5,137,780 | 8/1992 | Nichols et al. . |
| 5,167,876 | 12/1992 | Lem et al. . |
| 5,380,320 | 1/1995 | Morris ..................... 606/33 |
| 5,382,247 | 1/1995 | Cimino et al. ............. 606/33 |
| 5,395,312 | 3/1995 | Desai ........................ 604/22 |
| 5,562,659 | 10/1996 | Morris ..................... 604/41 |

FOREIGN PATENT DOCUMENTS

| | | |
|---|---|---|
| 63-129077 | 6/1988 | Japan . |
| 1445546 | 8/1976 | United Kingdom . |

OTHER PUBLICATIONS

Chmielewski et al., Philosophical Magazine A 43(3):739–751 (1981).

Parylene, A Biostable Coating for Medical Applications, Union Carbide Corporation (1993), 6 pages.

Parylene Literature Index, Union Carbide Corporation (1992), pp. 1–124.

*Primary Examiner*—Linda C. M. Dvorak
*Assistant Examiner*—Roy Gibson
*Attorney, Agent, or Firm*—Olson & Hierl, Ltd.

[57] ABSTRACT

A dielectric coating for electrosurgical instruments including a ceramic coating applied to the instrument and a parylene coating applied to the ceramic coating. The coating may be used on monopolar and bipolar electrosurgical instruments to provide insulation having good dielectric properties.

11 Claims, 5 Drawing Sheets

COMPOSITE DIELECTRIC COATING FOR ELECTROSURGICAL IMPLEMENTS

This application is a continuation of application Ser. No. 08/210,354, filed Mar. 18, 1994, abandoned.

FIELD OF THE INVENTION

This invention relates to improved electrosurgical implements, and particularly to composite dielectric coatings for mono-polar and bi-polar electrosurgical implements and devices.

BACKGROUND

The control of bleeding during surgery accounts for a major portion of the time involved in an operation. In particular, bleeding that occurs when tissue is incised or severed can obscure the surgeon's vision, prolong the operation, and adversely effect the precision of cutting. Blood loss from surgical-cutting may require blood infusion, thereby increasing the risk of harm to the patient.

It is known to use electrosurgical techniques to reduce bleeding from incised tissue. By using electrosurgical techniques, a high frequency or radio frequency current can be passed through the patient's tissue between two electrodes for both cutting and causing hemostasis in tissue. The current passing through the tissue causes joulean (ohmic) heating of the tissue as a function of the current density and the resistance of the tissue, and denatures the tissue proteins to form a coagulum that seals the bleeding sites.

Monopolar electrosurgical devices employ a small electrode at the end of a handle in the surgeon's hand and a large electrode plate beneath and in contact with the patient. Only one of the two electrodes required to complete the electrical circuit is manipulated by the surgeon and placed on or near the tissue being operated on. The other electrode is the large plate in contact with the patient. The electrosurgery power supply impresses high frequency voltage spikes of thousands of volts between these two electrodes, sufficient to cause an electric arcing from the small operating electrode the surgeon holds to the most proximate tissues, then through the patient to the large electrode plate contacting the patient. In the patient, the electrical current becomes converted to heat; hottest in the tissues immediately adjacent to the small hand-held electrode where the currents are most concentrated.

In bipolar electrosurgical devices, two electrodes are closely spaced together and have the same surface area in contact with the tissue. The current flow is thus locally confined to the tissue that is disposed between and electrically connects the electrodes.

Because of the dangers associated with the use of electrical instruments during surgery, special properties are required of the instruments. For example, it is known to use parylene as a conformal coating for the electrosurgical instruments. It is unique as a coating because of its ability to provide ultra-thin films and conform to substrates of varied geometrical shapes and irregularities. Parylene has excellent chemical resistance and can be used at relatively high temperatures.

Parylene is a generic term applied to the family of unsubstituted and substituted poly(p-xylylenes). The polymers can be homopolymers or co-polymers depending on whether they are derived from one particular dimer or a mixture of different cyclic dimers. In general, these cyclic dimers have the following structural formula,

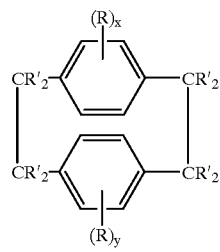

wherein R is a substituent on the aromatic ring, x and y are each integers from 0 to 3, inclusive, R' is H, Cl or F. Typical R groups include hydrogen, hydrocarbon, oxyhydrocarbon, thiohydrocarbon, hydroxyl, halogen, nitro, nitrile, amine and mercapto groups. After these cyclic dimers are pyrolized, they may be in the form of diradicals having the structures

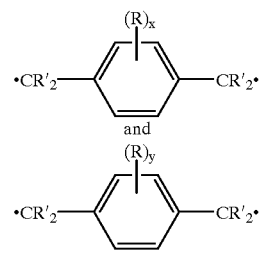

or moieties having the tetraene or quinoid structures represented by the formulas,

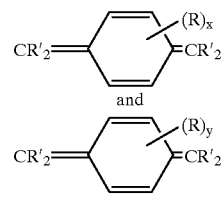

According to the patent literature, it may be that the tetraene or quinoid structure is the dominant structure which results when the cyclic dimer is pyrolyzed, but that the monomer polymerizes as though it were in the diradical form. As previously discussed, the preparation of these cyclic par-axylylene dimers and their pyrolytic cleavage and subsequent condensation to form copolymers and homopolymers is well known and described in the patent literature, particularly U.S. Pat. Nos. 3,149,175, No. 3,342,754, No. 3,288,728, No. 3,246,627, No. 3,301,707, No. 3,600,216 and No. 4,291,245 all of which patents are incorporated by reference herein.

Parylene coatings can be made from commercially available starting materials such as Parylene N, Parylene C, and Parylene D.

Parylene N coatings are produced by vaporizing di(p-xylylene) dimer, pryolyzing the vapor to produce p-xylylene free radicals, and condensing a polymer from the vapor onto a substrate that is maintained at a relatively low temperature, typically ambient or below ambient. Parylene N is derived from di(p-xylylene), while parylene C is derived from di(monochloro-p-xylylene), and parylene D is derived from di(dichloro-p-xylylene).

Although parylenes have generally advantageous electrical, chemical resistance and moisture barrier properties, it has been found that these polymers do not adhere well to many substrate surfaces, particularly under wet conditions. Although these polymers are quite resistant to liquid water under most conditions, they are subject to penetration by water vapor which may condense at the interface between the parylene film and the substrate, forming liquid water which tends to delaminate the film from the substrate. Vapor deposited parylene films are also generally quite crystalline and are subject to cracking which may also create undesirable paths for penetration of moisture to the substrate surface.

It is also known to use ceramic coatings on electrosurgical instruments because of the unique properties of ceramic. Unlike metals, which have relatively high thermal conductivity, ceramic coatings are noted for their thermal barrier properties. However, ceramic coatings tend to be porous and develop cracks making such coatings less than ideal for electrosurgical applications.

It is an object of the present invention to provide an improved dielectric coating for electrosurgical implements.

It is a further object of the present invention to provide such a dielectric coating that reduces the likelihood of capacitative build-up of current during electrosurgery.

SUMMARY OF THE INVENTION

In accordance with these and other objects, a composite dielectric coating for electrosurgical implements is provided. In its preferred embodiment, the coating comprises a ceramic coating applied to the implement, and a parylene coating applied over the ceramic. Because of its porosity, the ceramic coating merges with the parylene coating along an irregular surface. As a result of this irregular surface, the porous structure of the ceramic is filled with polymer. Thus, the resulting composite coating not only does not permit entry of moisture but also strengthens the dielectric coating as well. The present composite dielectric coating may be used on monopolar and bipolar electrosurgical instruments and appliances.

DETAILED DESCRIPTION OF THE PREFERRED EMBODIMENTS

Figure 1:
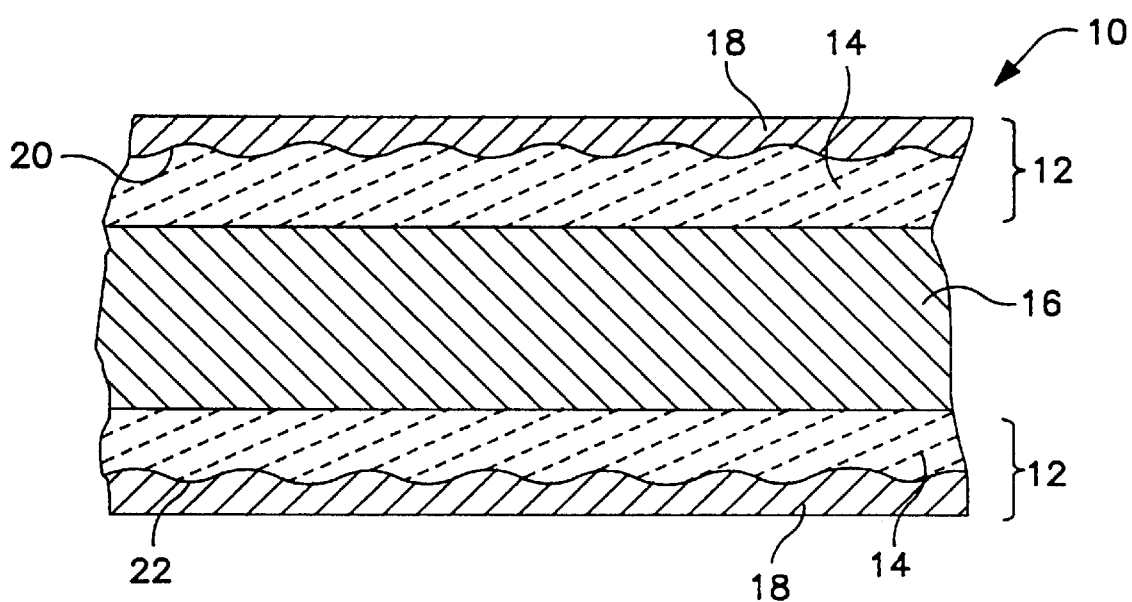
FIG. 1. is a cross sectional view of an electrosurgical device, taken along its longitudinal axis, illustrating a composite dielectric coating in accordance with a preferred embodiment of the invention.

Referring to the drawings FIG. 1 shows the cross section of an electrosurgical implement segment 10 having a dielectric coating 12 in accordance with the preferred embodiment. The dielectric coating comprises a porous ceramic layer 14 applied to the metallic substrate 16 of the implement and a parylene coating 18 applied to the ceramic layer. Because of the porosity of the ceramic layer, the parylene and ceramic layers merge along an irregular surface 20 and parylene extends into the pores of the ceramic layer. Depending upon the porosity of the applied ceramic layer, parylene can also extend through the porous ceramic layer.

The ceramic coating is applied to an electrosurgery instrument as follows. First, the substrate metal of the instrument is cleaned of all grease and other contaminants. This can be done in an ultrasonic bath of alcohol, acetone, or other appropriate cleaner.

Next, the substrate surface is abraded (roughened), e.g., by grit blasting, preferably with an aluminum oxide grit. This provides a desirable topography for the applied ceramic powder to grasp. The substrate then is cleaned again in an ultrasound bath to remove any remaining pieces of grit from the grit blasting process, as well as any other contaminants that may have been interjected.

Then, using suitable fixturing, preheated ceramic powder is applied by means of a thermal spray device. The fixturing is of such a nature as to keep the substrate steady and accessible to the spray device nozzle during the spraying process. The fixture is of such design as to permit manipulation, spinning, moving and/or holding steady the item being sprayed. The spray device is mounted so that it can traverse before, over, behind, under, and/or around the item being sprayed in order to deposit a substantially uniform coating.

The ceramic powder is preferably aluminum oxide. Other appropriate ceramic powders are mixtures of aluminum oxide and titanium oxide, and the like. Suitable such other coatings are described in U.S. Pat. No. 4,726,368 to Morris. The particle size preferably is about 1 to 2 microns, although particle sizes up to 100 microns can be used depending upon the desired characteristics of the final product plus the geometries of the item being sprayed.

Smaller micron size powders produce a denser coating of relatively higher dielectric strength. Grain boundaries between the alumina particles are diminished. With relatively finer powders, the resulting coating exhibits greater adhesion and resistance to residual stress. Preferably the ceramic powder is deposited in multiple passes at a rate of about 0.00025" to 0.002" of coating thickness per pass, to an overall coating thickness of about 0.001" to about 0.030", depending upon the design of the instrument, the desired dielectric strength, and the intended use of the instrument.

Control of substrate temperature is desirable in some instances. To that end, substrate cooling can be accomplished by jets of air directed at the item being sprayed, or by a coolant being introduced into a hollow substrate during the thermal spraying process. Cooling of the ceramic-coated item is done relatively slowly so as to avoid micro-cracks in the produced ceramic coating.

Several iterations of powder deposition are possible. One iteration is for the aluminum oxide powder coating to be applied extremely densely, with less than 4% porosity. Parylene [poly(p-xylylene)] is then applied to the ceramic layer, achieving a penetration of the relatively dense ceramic layer. This combination establishes surface hydrophobicity by substantially eliminating any tortuous paths to substrate along any grain boundaries or through pores. By preventing a path for water and water borne ions, or conductive compounds, to the substrate, the overall dielectric strength of the produced composite coating is enhanced.

Another iteration is to spray a dense base coating (up to 5% porosity) to a thickness of about 0.001" to 0.015". Then a top ceramic coating is applied to the first coating. The top coating is purposely sprayed to be more porous than the base coating. Parylene [poly(p-xylylene)] is then applied to the ceramic top coating, achieving a penetration of the top, more porous layer of ceramic, thereby achieving hydrophobicity and dielectric strength similar to that described above.

Yet another iteration is to initially apply to the substrate a base coat of molybdenum about 0.001" to 0.002" thick before application of a thicker layer (0.005" to 0.050") of aluminum oxide, with less than 4% porosity. Parylene is then applied to the ceramic, again achieving the hydrophobicity and dielectric strength as described above.

Still another iteration combines the foregoing coating process with the application of a top, more porous layer as described above.

The overall process for coating the ceramic layer with parylene is as follows. First, a cyclic dimer containing the desired repeating unit, e.g., cyclic di-p-xlylene, is heated to a temperature of about 100° C. to about 200° C. at a pressure of about 1 to about 100 microns. Then, by pyrolyzing the vaporized cyclic dimer at slightly lower pressure and at about 6000C. to about 750° C., the pyrolysis step breaks the benzylic carbon-to-carbon bonds to provide a reactive p-xylylene monomer in vapor state. Finally, upon introducing the vaporous monomer into a deposition chamber containing the substrate, at still slightly lower pressure, but at ambient temperatures in the range of about 20° C. to about 30° C., the monomer condenses and polymerizes on all of the exposed surfaces of the substrate to provide a thin parylene film. A slight pressure gradient is established throughout the process, with the pressure progressively getting lower in each stage. This established pressure differential drives the monomer vapor from one stage of the process to the next.

The apparatus used typically comprises a vaporizer or sublimator section, a pyrolysis zone, and a deposition or condensation chamber, all connected. The deposition chamber is provided with a valved outlet connected to a pump for providing the required reduced pressure. Heating means for vaporization and pyrolysis are provided as well. Condensation is effected at about ambient temperature as described above.

Preferably, the poly(p-xylylene) coating is deposited onto the ceramic coating under vacuum in an enclosure having three temperature zones—a relatively low temperature zone, an intermediate temperature zone, and a relatively high temperature zone. The relatively low temperature zone (condensation zone) is maintained at about ambient temperature, the intermediate temperature zone (sublimination zone) is maintained at about 100 to 150° C., and the relatively high temperature zone (dissociation zone) is maintained at a temperature in the range of about 650° to about 740° C.

The ceramic-sheathed electrosurgery implement to be coated is positioned in the condensation zone and the p-xylylene dimer (preferably Parylene C) in the form of a white powder is introduced into the sublimination zone. As high vacuum is drawn on the system (usually about 1 micron Hg pressure), the dimer sublimes and is passed into the dissociation zone where the dimer is cleaved into a reactive monomer precursor of poly(p-xylylene). From the dissociation zone the reactive monomer enters the condensation zone, permeates into the pores of the ceramic sheath of the electrosurgery implement and condenses thereon to form a polymeric film coating over the ceramic sheath.

For relatively dense ceramic coatings (i.e., porosity less then about 1 percent), Parylene C is the preferred starting material. For relatively porous ceramic coatings, on the other hand, Parylene N is the preferred starting material because of its superior penetrating capability into restricted regions such as pores and cracks.

Figure 4:
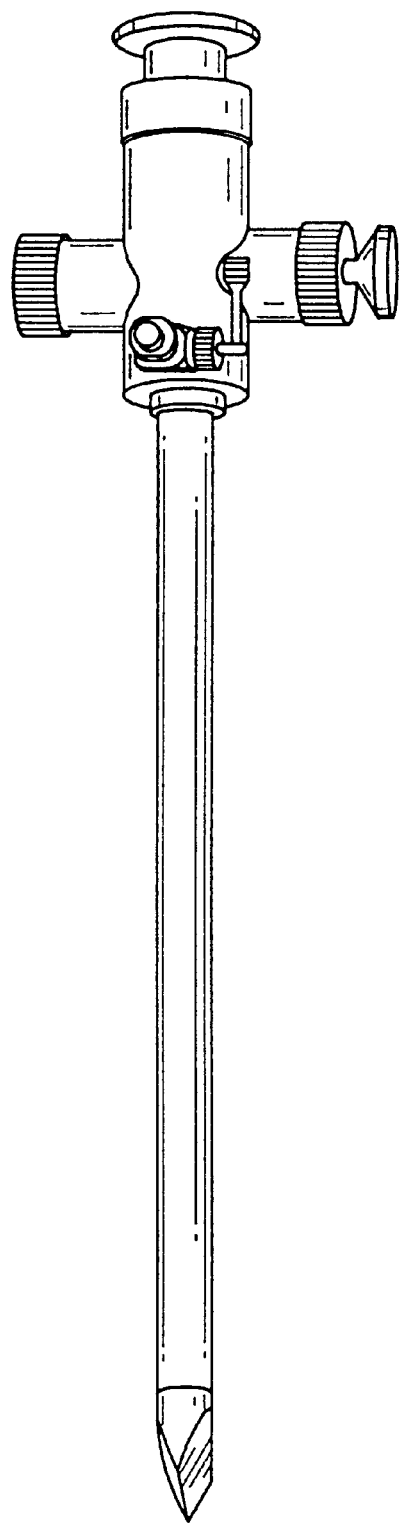
FIG. 4 is a trocar with an insulated shaft coated with a dielectric coating embodying the present invention.
Figure 5:
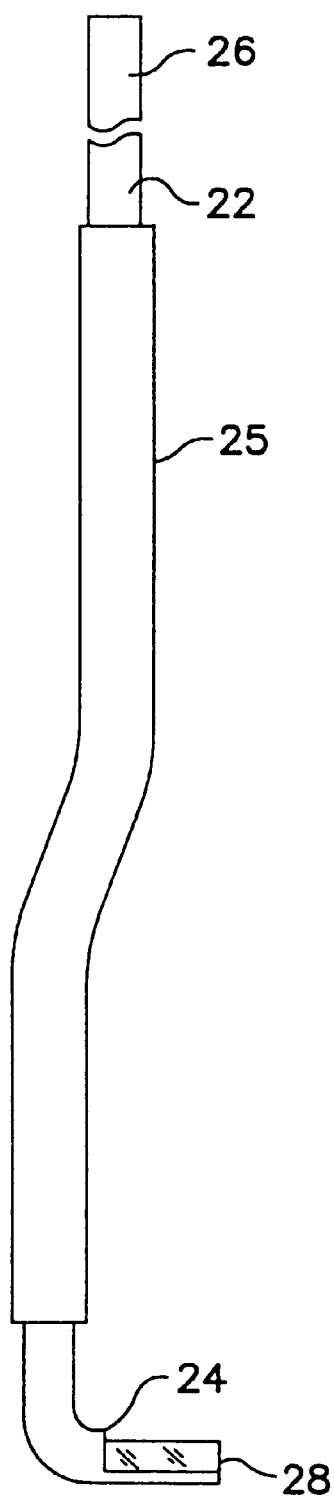
FIG. 5 is a side view of an electrosurgical device having a hook electrode tip.

The above-described composite dielectric coating may be used with all types of electrosurgical implements, monopolar as well as bipolar devices, to provide the necessary insulation. For example, a typical electrode embodying the present invention in a bipolar electrosurgery device is shown in FIG. 4 where shank 22 of stainless steel hook electrode 24 is provided with a composite ceramic/poly(p-xylylene) coating 25 about 0.005 inch thick. The proximate end 26 of shank 22 is exposed stainless steel adapted for operable connection to an appropriate high-frequency power source. The distal end 28 of electrode 24 is also conductive and may be contoured in a hook shape.

Figure 2E:
FIGS. 2(a) through 2(f) illustrate various electrode tips the shafts of which are coated with a composite dielectric coating embodying the present invention.
Figure 2F:
Figure 2C:
Figure 2D:
Figure 2A:
Figure 2B:

The presently contemplated composite dielectric coating may, for example, be used with devices terminating in a knife tip (FIG. 2(a)), a cone tip (FIG. 2(b)), a hook tip (FIG. 2(c)), a button tip (FIG. 2(d)), a spatula tip (FIG. 2(e)), or a sling tip (FIG. 2(f)). The coating can also be used with trocars (FIG. 4) and similar implements.

Figure 3:
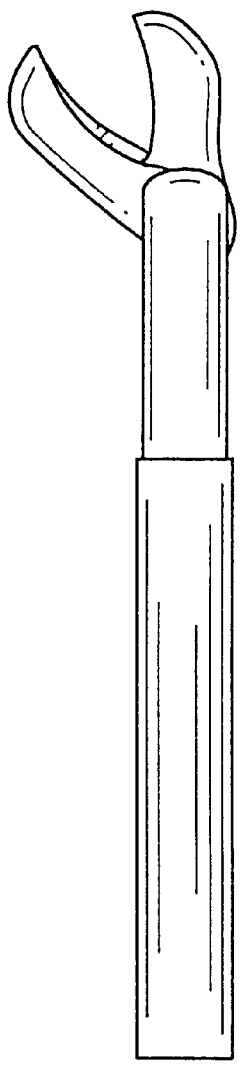
FIG. 3 is a scissor electrode tip having a shaft coated with a dielectric coating embodying the present invention.

The coating can also be used with monopolar and bipolar electrosurgical scissors (FIG. 3). Desirably, the dielectric coating on the bipolar electrosurgical scissors extends to the scissor members themselves, except for the cutting edges of the scissors. In the case of monopolar electrosurgical scissors only the shank is provided with a dielectric coating.

The dielectric strength in any given instance can be modulated by adjusting the thickness of the composite coating and also by the relative amounts of ceramic and parylene present in the coating. For bipolar implements the preferred dielectric strength (i.e., absence of arcing) is at least 1000 volts regardless of frequency, preferably at least 1,500 volts.

Figure 6:
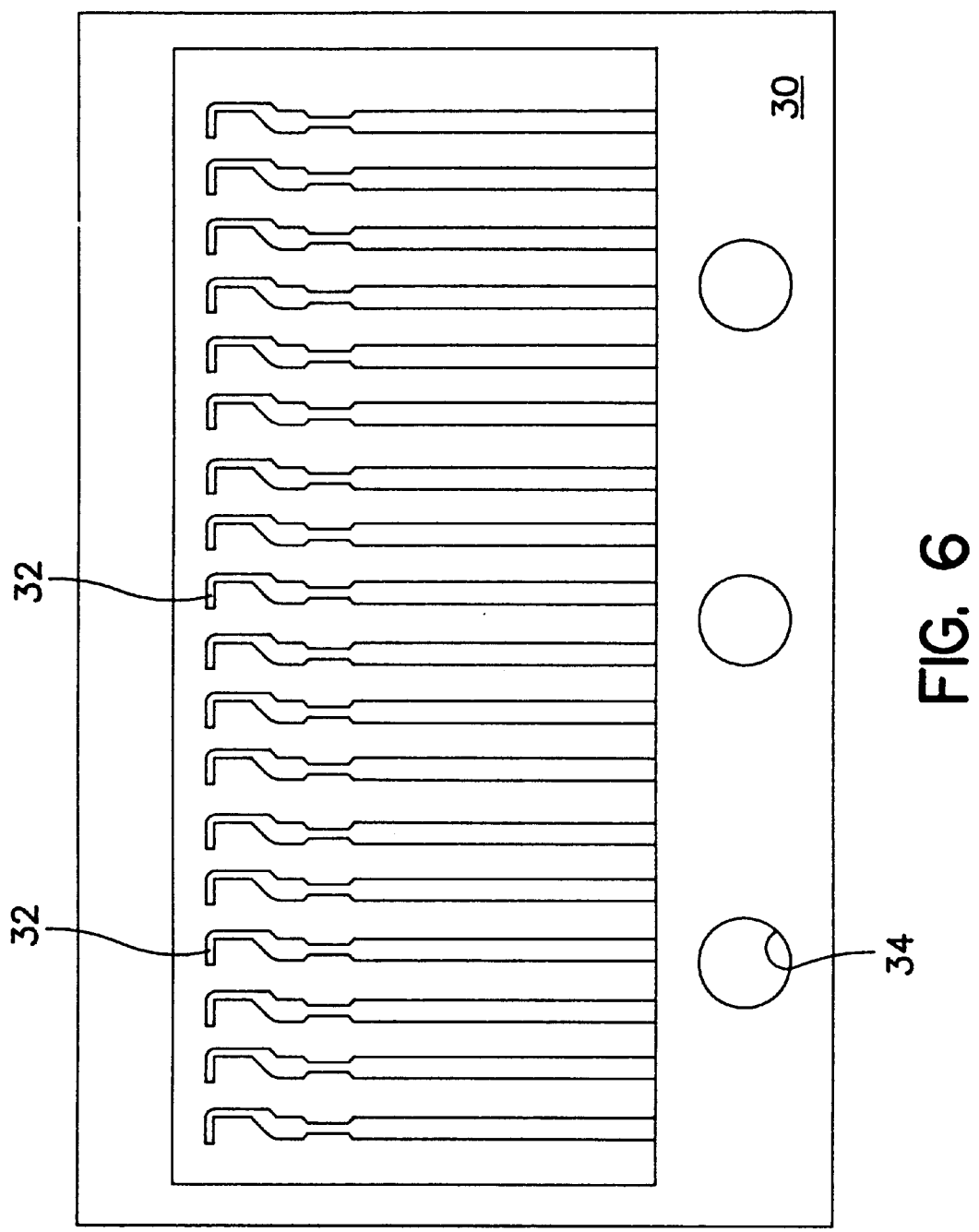
FIG. 6 is an elevational view of a card comprising a plurality of hook electrode tips, the card illustrating an expedient for mass manufacturing electrode tips embodying the invention.

As a manufacturing expedient, a plurality of tips of FIGS. 2(a)–2(f) can be initially formed in a card and then be coated together as a group. FIG. 6 shows such a card 30 comprising a plurality of hook tip electrodes 32 unitary therewith. Card 30 is also provided with fixture mounting apertures 34.

The foregoing description and the accompanying drawings are intended as illustrative but not limiting. Still other variations and rearrangements of parts are possible without departing from the spirit and scope of the present invention.

We claim:

1. An electrosurgical implement comprising an electrode with a metallic substrate provided with a dielectric coating having a dielectric strength of at least 1000 volts on a portion of said substrate, said dielectric coating being constituted by a porous ceramic layer at least about 0.001 inch thick, contiguous with said metallic substrate and a poly (p-xylylene) layer over said ceramic layer and substantially sealing the porous ceramic layer and penetrating into the pores thereof, said ceramic layer and said poly (p-xylylene) layer merging into one another along an irregular interface.

2. The electrosurgical implement in accordance with claim 1 wherein said ceramic layer is an alumina layer.

3. The electrosurgical implement in accordance with claim 1 which is a hook-tip electrode.

4. The electrosurgical implement in accordance with claim 1 which is scissors.

5. The electrosurgical implement of claim 1 further comprising a cone electrode tip.

6. The electrosurgical implement of claim 1 further comprising a button electrode tip.

7. The electrosurgical implement of claim 1 further comprising a spatula electrode tip.

8. The electrosurgical implement of claim 1 further comprising a sling electrode tip.

9. The electrosurgical implement of claim 1 wherein the implement is a trocar instrument.

10. An article of manufacture for electrosurgical instruments, the article comprising a plurality of electrosurgical implements unitary with a sheet-form frame that surrounds said implements, each implement comprising an electrode with a metallic substrate and a dielectric coating having a dielectric strength of at least 1000 volts on a portion of the substrate;

the dielectric coating being constituted by a porous ceramic layer contiguous with the metallic substrate and a parylene layer over the ceramic layer;

the ceramic layer and the parylene layer merging along an irregular interface and the parylene layer extending into the pores of the ceramic layer and substantially sealing the ceramic layer.

11. The article of manufacture of claim 10 wherein each implement comprises a hook tip electrode.

* * * * *